(12) United States Patent
Venkataramani et al.

(10) Patent No.: US 12,239,484 B2
(45) Date of Patent: Mar. 4, 2025

(54) MEDICAL IMAGING METHOD

(71) Applicant: GE Precision Healthcare LLC, Wauwatosa, WI (US)

(72) Inventors: Rahul Venkataramani, Karnataka (IN); Chandan Aladahalli, Karnataka (IN); Krishna Seetharam Shriram, Karnataka (IN); Vikram Melapudi, Karnataka (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 101 days.

(21) Appl. No.: 17/646,085

(22) Filed: Dec. 27, 2021

(65) Prior Publication Data

US 2023/0200778 A1 Jun. 29, 2023

(51) Int. Cl.
*A61B 8/00* (2006.01)
*G06V 10/82* (2022.01)

(52) U.S. Cl.
CPC ............ *A61B 8/4254* (2013.01); *A61B 8/461* (2013.01); *A61B 8/463* (2013.01); *G06V 10/82* (2022.01)

(58) Field of Classification Search
CPC ....... A61B 8/08; A61B 8/4245; A61B 8/4254; A61B 8/46; A61B 8/463; A61B 8/469; A61B 8/54; G06N 3/08; G06N 5/022; G06N 5/04
See application file for complete search history.

(56) References Cited

U.S. PATENT DOCUMENTS

| | | | |
|---|---|---|---|
| 10,140,710 B2 | 11/2018 | Kreeger | |
| 10,702,248 B2 | 7/2020 | Vignon et al. | |
| 10,964,424 B2 | 3/2021 | Pagoulatos et al. | |
| 11,593,638 B2 | 2/2023 | Kezurer et al. | |
| 2018/0153505 A1 | 6/2018 | Cadieu et al. | |
| 2019/0354856 A1* | 11/2019 | Kezurer | G16H 50/20 |
| 2020/0113542 A1 | 4/2020 | Perrey et al. | |
| 2022/0189041 A1* | 6/2022 | Cauley | G01R 33/56509 |
| 2022/0225963 A1* | 7/2022 | Sutton | A61B 8/5269 |

OTHER PUBLICATIONS

Thomas Szabo "Diagnostic Ultrasound Imaging: Inside Out" Chapter 10 "Imaging systems and Applications", 2014 (Year: 2024).*
Oden Technology, "What is Model Training?", 2024 (Year: 2024).*
Hocreiter, S. et al., "Flat Minima," Neural Computation, vol. 9, No. 1, Jan. 1997, 38 pages.

(Continued)

*Primary Examiner* — Boniface N Nganga
*Assistant Examiner* — Brooke Lyn Klein
(74) *Attorney, Agent, or Firm* — McCoy Russell LLP

(57) ABSTRACT

Methods and systems are provided for generating ultrasound probe motion recommendations. In one example, a method includes obtaining an ultrasound image of a source scan plane, the ultrasound image acquired with an ultrasound probe at a first location relative to a patient, entering the ultrasound image as input to a probe recommendation model trained to output a set of recommendations to move the ultrasound probe from the first location to a plurality of additional locations at which a plurality of target scan planes can be imaged, and displaying the set of recommendations on a display device.

12 Claims, 6 Drawing Sheets

(56) References Cited

OTHER PUBLICATIONS

Keskar, N. et al., "On Large-Batch Training for Deep Learning: Generalization Gap and Sharp Minima," arXiv Cornell University Website, Available Online at https://arxiv.org/abs/1609.04836, Available as Early as Sep. 15, 2016, Last Revised Feb. 9, 2017, 16 pages.

Izmailov, P. et al., "Averaging Weights Leads to Wider Optima and Better Generalization," arXiv Cornell University Website, Available Online at https://arxiv.org/abs/1803.05407, Available as Early as Mar. 14, 2018, Last Revised Feb. 25, 2019, 12 pages.

Alansary, A. et al., "Automatic View Planning with Multi-scale Deep Reinforcement Learning Agents," arXiv Cornell University Website, Available Online at https://arxiv.org/abs/1806.03228, Available as Early as Jun. 8, 2018, 8 pages.

Li, Y. et al., "Fast Multiple Landmark Localisation Using a Patch-based Iterative Network," arXiv Cornell University Website, Available Online at https://arxiv.org/abs/1806.06987, Available as Early as Jun. 18, 2018, Last Revised Oct. 7, 2018, 8 pages.

Droste, R. et al., "Automatic Probe Movement Guidance for Free-hand Obstetric Ultrasound," arXiv Cornell University Website, Available Online at https://arxiv.org/abs/2007.04480, Available as Early as Jul. 8, 2020, 10 pages.

Yeung, P. et al., "Learning to map 2D ultrasound images into 3D space with minimal human annotation," Medical Image Analysis, vol. 70, May 2021, 15 pages.

\* cited by examiner

MEDICAL IMAGING METHOD

TECHNICAL FIELD

Embodiments of the subject matter disclosed herein relate to medical imaging.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In one embodiment, a method includes obtaining an ultrasound image of a source scan plane, the ultrasound image acquired with an ultrasound probe at a first location relative to a patient, entering the ultrasound image as input to a probe recommendation model trained to output a set of recommendations to move the ultrasound probe from the first location to a plurality of additional locations at which a plurality of target scan planes can be imaged, and displaying the set of recommendations on a display device.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
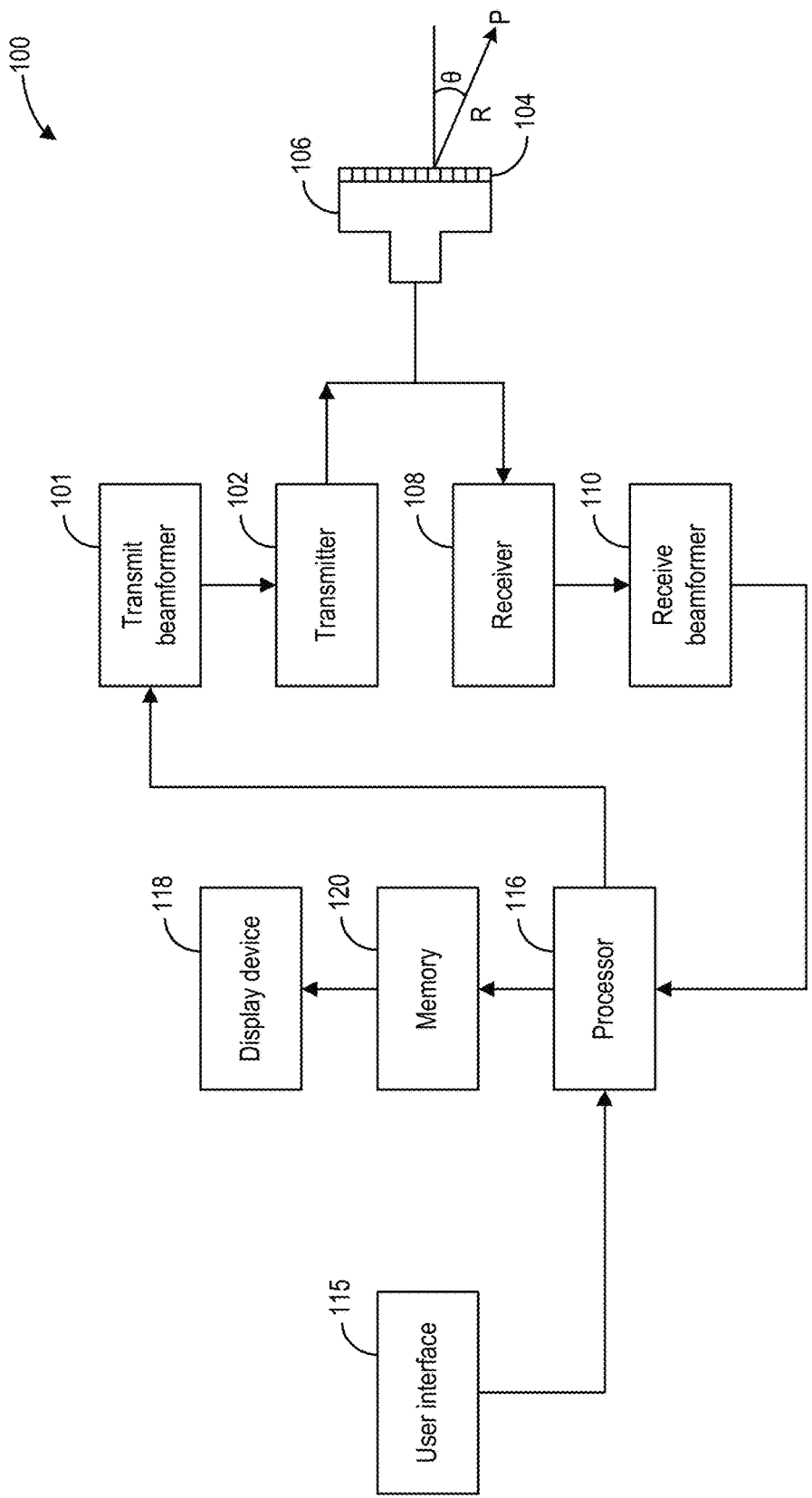
FIG. 1 shows a block diagram of an embodiment of an ultrasound system.

Medical ultrasound imaging typically includes the placement of an ultrasound probe including one or more transducer elements onto an imaging subject, such as a patient, at the location of a target anatomical feature (e.g., abdomen, chest, etc.). Images are acquired by the ultrasound probe and are displayed on a display device in real time or near real time (e.g., the images are displayed once the images are generated and without intentional delay). The operator of the ultrasound probe may view the images and adjust various acquisition parameters and/or the position of the ultrasound probe in order to obtain high-quality images of one or more target anatomical features (e.g., the heart, the liver, the kidney, or another anatomical feature).

Ultrasound scans may include the imaging of one or more scan planes, which may be standardized based on known human anatomy. For example, an ultrasound scan of the kidney may include the right kidney mid-axial plane as a target/standard scan plane. Besides the commonly-used standard scan planes, arbitrary planes may be used as targets within the underlying anatomy. Imaging a target scan plane involves moving the ultrasound probe from the current location to a location where the target scan plane can be visualized and, in some examples, rotating the probe in one or more of three independent directions (e.g. pitch, roll, and yaw). In many cases, scan protocols may dictate that multiple scan planes be imaged to gather sufficient diagnostic images of the underlying anatomy. For example, if a kidney is to be imaged, it may be desired to collect data from both the mid-axial and mid-longitudinal planes of the kidney.

Moving the ultrasound probe to the proper location(s) to acquire images of the target anatomical feature(s) in the correct scan plane(s) may be challenging and is based on user experience. Thus, probe motion guidance may be provided to aid the operator of the ultrasound probe to properly position the ultrasound probe. Traditional approaches to guidance of ultrasound probe position have relied on zeroth order information about the current view or the current position of the probe. Typically, this involves estimating the probe position (e.g., based on anatomical features identified in a current image frame) and recommending probe movement based on the estimated probe position relative to a target probe position. These probe motion recommendations may be generated by a model trained to output probe motion guidance to move the probe from the current position to the target probe position at which a target scan plane can be imaged.

However, some scan protocols include more than one target scan plane. When probe motion recommendations are generated to guide an ultrasound operator to scan multiple target scan planes, the above-described methods of generating guidance may rely on multiple, separate models that independently recommend separate probe motions to move the ultrasound probe to a first target scan plane and to a second target scan plane (e.g., as each probe recommendation may be generated by a separate model). These independent recommendations may result in inefficient probe motion, or in some cases, conflicting probe motion guidance that may be infeasible for the operator to follow. As such, the probe motion recommendations may actually result in excessive scan times and operator confusion. As a result, the probe motion guidance provided from the multiple models may not be consistent with each other and may result in unnecessary or incorrect probe motion, thereby frustrating the purpose of the probe motion guidance.

Thus, according to embodiments described herein, probe motion/placement recommendations to scan two or more different target scan planes may be generated with a single probe recommendation model trained to output a set of recommendations, rather than each of two or more independent models generating separate probe motion recommendations. The probe recommendation model according to the present disclosure for generating probe motion recommendations may be improved through the enforcement of anatomical spatial consistency in the recommendations. Given a source scan plane (e.g. the plane currently being imaged by a user), probe motion recommendations may be generated for each target scan plane simultaneously, comprising motion from the source plane to one or more target scan planes, such that imagery from within each scan plane may be acquired. The probe recommendations may be generated by the single model at the same time, with anatomical spatial consistency enforced through a loss function which penalizes anatomical inconsistency. Adding anatomical consistency information to the training data of the joint probe movement recommendation model may eliminate or reduce instances of contradictory or infeasible probe movement recommendations. It may also improve the robustness of the recommendations, allowing for faster exam times and reduced operator cognitive load.

Instead of, or in addition to, the anatomical inconsistency terms present in the loss function, the training data itself may have anatomical spatial consistency information added. Training data for the disclosed method may comprise, for example, sets of sequences of images of scan planes, the 3D locations of those scan planes, and transformations (e.g., in the form of transformation matrices) between the scan planes within the sequences. The transformation matrices may be chosen by experts, such that the anatomical consistency of the anatomy is respected, e.g. that no anatomical contradictions are present within the transformation matrices.

Figure 3:
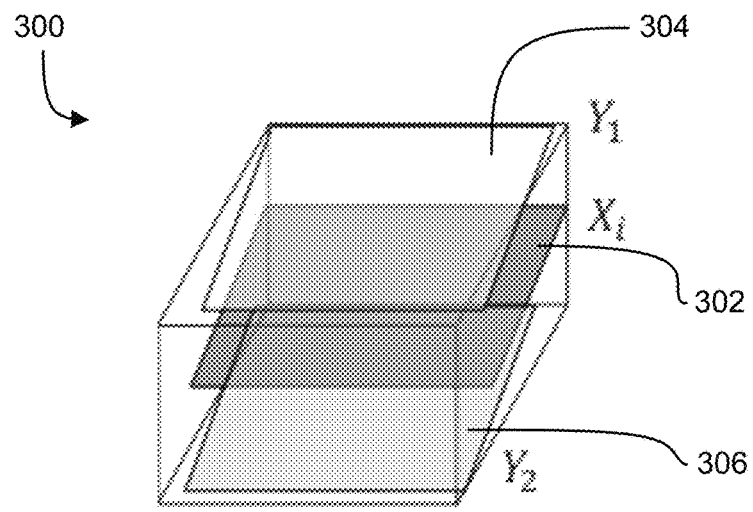
FIG. 3 schematically shows an example source scan plane and two target scan planes.
Figure 4:
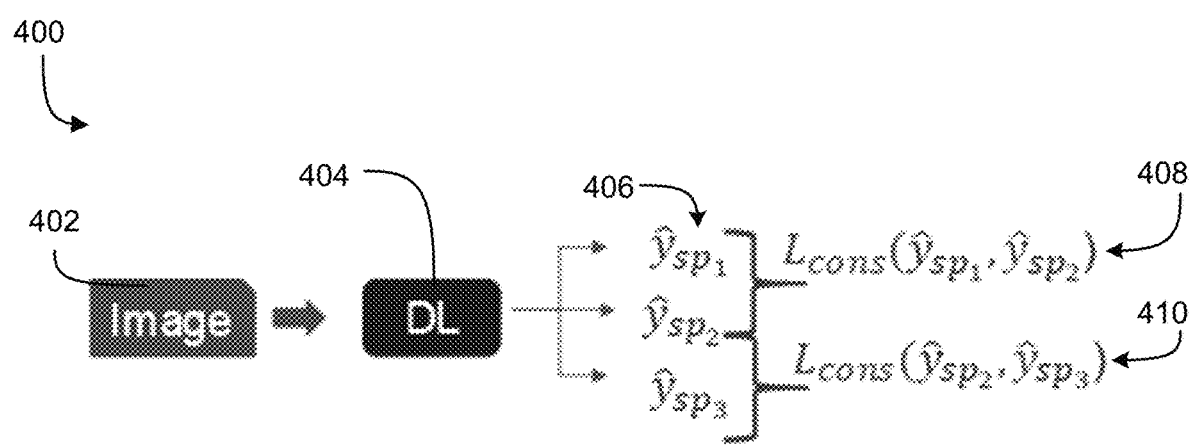
FIG. 4 schematically shows an example process for calculating loss functions during training of a probe recommendation model.
Figure 5:
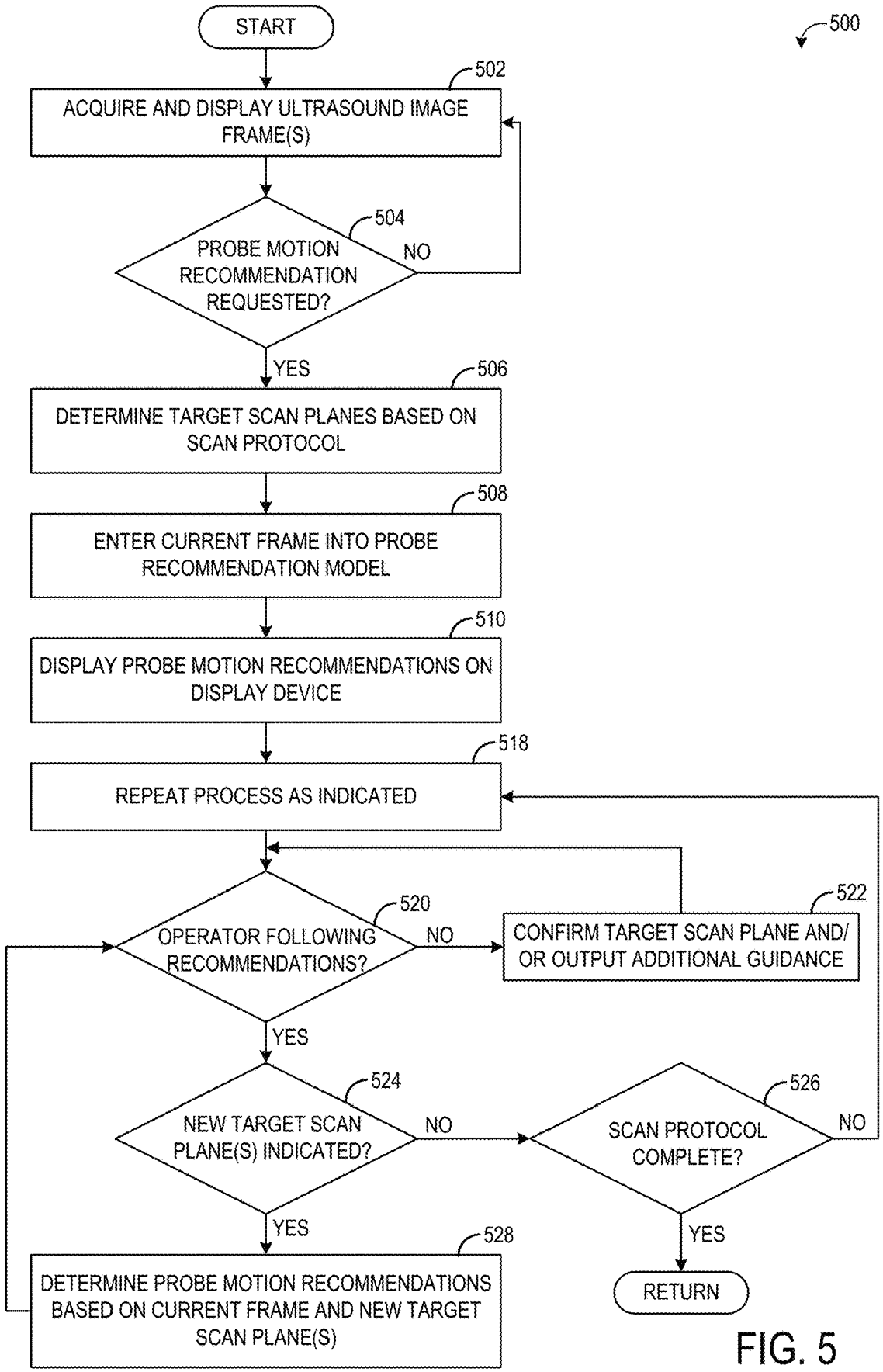
FIG. 5 is a flow chart illustrating a method for generating joint probe motion recommendations with a probe recommendation model, according to an embodiment of the present disclosure.
Figure 6:
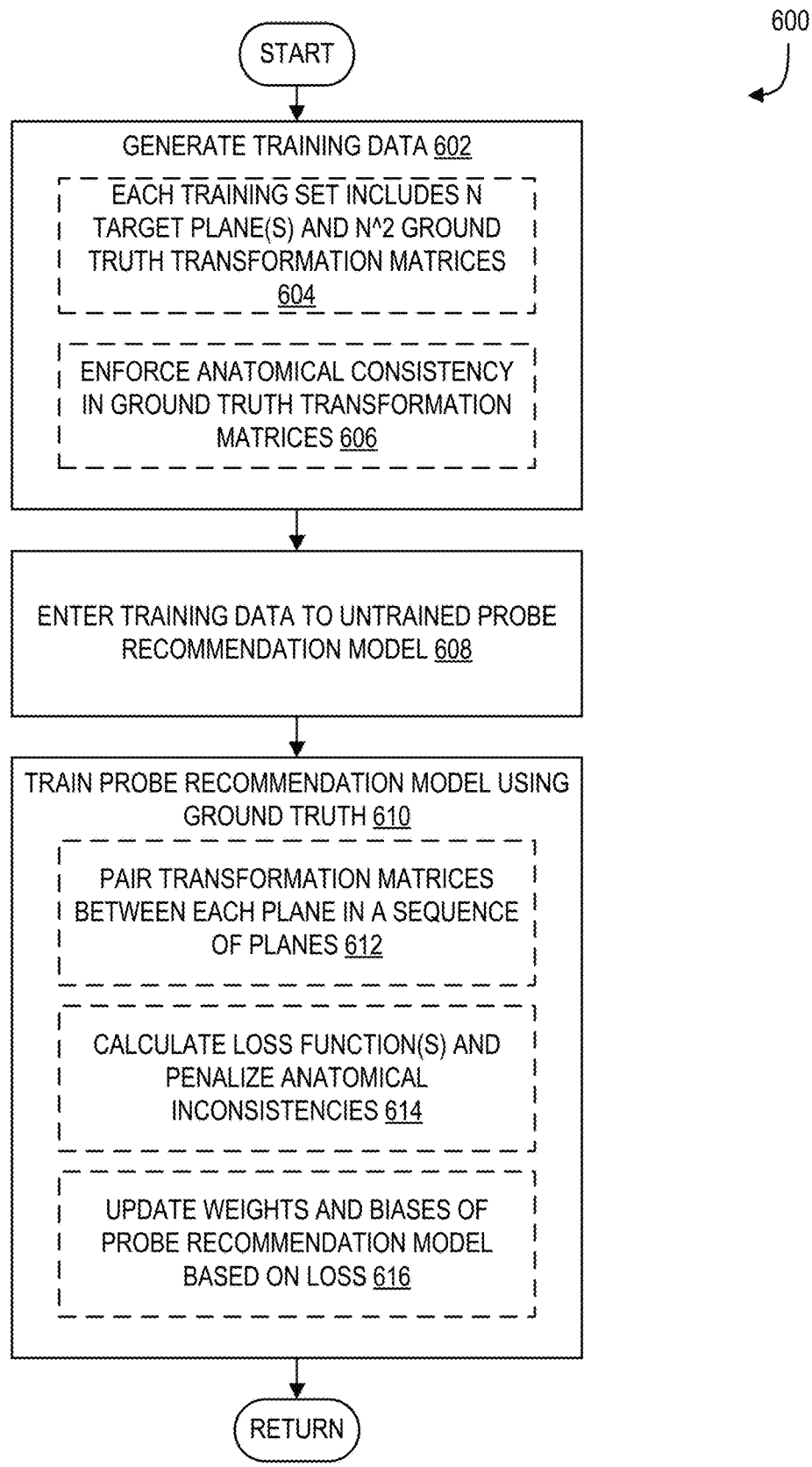
FIG. 6 is a flow chart illustrating a method for training a probe recommendation model, according to an embodiment of the present disclosure.
Figure 7:
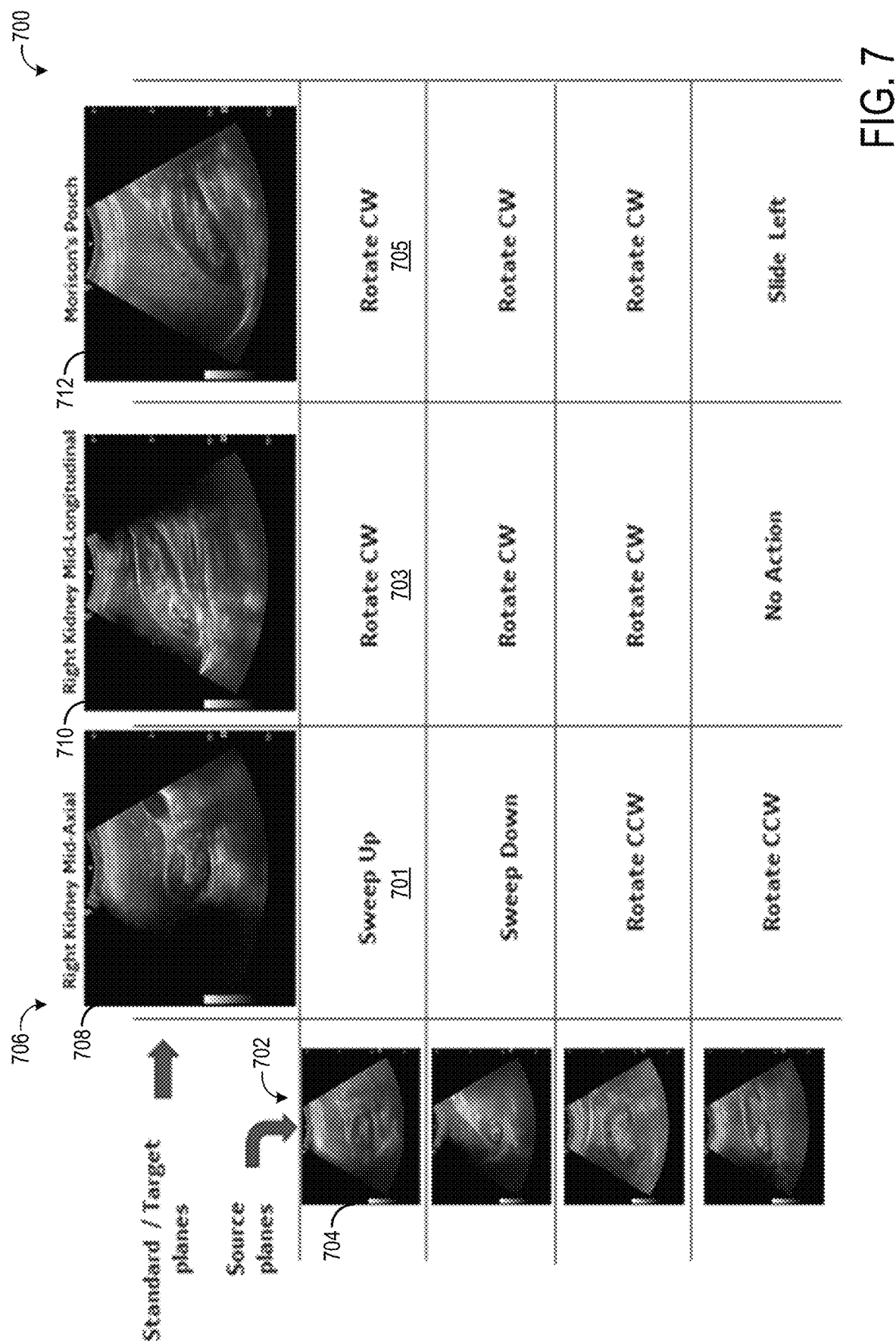
FIG. 7 shows example probe recommendations that may be output by a trained probe recommendation model.

An example ultrasound system including an ultrasound probe, a display device, and an imaging processing system are shown in FIG. 1. Via the ultrasound probe, ultrasound data may be acquired and ultrasound images may be displayed on the display device. The ultrasound images may be processed by an image processing system, such as by the image processing system of FIG. 2, to determine probe motion guidance to guide an operator of the ultrasound probe to move the probe to two or more target scan planes. FIG. 3 shows an example current imaging frame (e.g., a source scan plane) and two possible target scan planes. FIG. 4 shows an example deep learning model trained to output joint probe guidance recommendations using multiple loss functions. FIG. 5 shows an example method for outputting probe motion guidance to multiple target scan planes. FIG. 6 is a flow chart illustrating a method for training a deep learning model to generate probe motion guidance. FIG. 7 illustrates examples of probe motion guidance that may be generated to guide an operator from various scan planes to various target scan planes.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic wave. In this way, transducer elements 104 may convert electronic transmit signals into acoustic transmit beams.

After the elements 104 of the probe 106 emit pulsed ultrasonic signals into a body (of a patient), the pulsed ultrasonic signals reflect from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data.

The echo signals produced by transmit operation reflect from structures located at successive ranges along the transmitted ultrasonic beam. The echo signals are sensed separately by each transducer element and a sample of the echo signal magnitude at a particular point in time represents the amount of reflection occurring at a specific range. Due to the differences in the propagation paths between a reflecting point P and each element, however, these echo signals are not detected simultaneously. Receiver 108 amplifies the separate echo signals, imparts a calculated receive time delay to each, and sums them to provide a single echo signal which approximately indicates the total ultrasonic energy reflected from point P located at range R along the ultrasonic beam oriented at the angle $\theta$.

The time delay of each receive channel continuously changes during reception of the echo to provide dynamic focusing of the received beam at the range R from which the echo signal is assumed to emanate based on an assumed sound speed for the medium.

Under direction of processor 116, the receiver 108 provides time delays during the scan such that steering of receiver 108 tracks the direction $\theta$ of the beam steered by the transmitter and samples the echo signals at a succession of ranges R so as to provide the time delays and phase shifts to dynamically focus at points P along the beam. Thus, each emission of an ultrasonic pulse waveform results in acquisition of a series of data points which represent the amount of reflected sound from a corresponding series of points P located along the ultrasonic beam.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the real RF (radio-frequency) data and generates complex data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of less than optimal or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be analyzed by one or more machine learning models trained using ultrasound images and corresponding ground truth output in order to identify the current scan plane and generate probe motion recommendations for moving the probe to image one or more target scan planes. As used herein, ground truth output refers to an expected or "correct" output based on a given input into a machine learning model. For example, if a machine learning model is being trained to classify images of cats, the ground truth output for the model, when fed an image of a cat, is the label "cat". As explained in more detail below, if a machine learning model is being trained to output probe motion recommendations on the basis of a source scan plane and two or more target scan planes, the ground truth output for the model may be transformations representing expert-confirmed probe motion to scan the two or more target scan planes starting from the source scan plane.

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Figure 2:
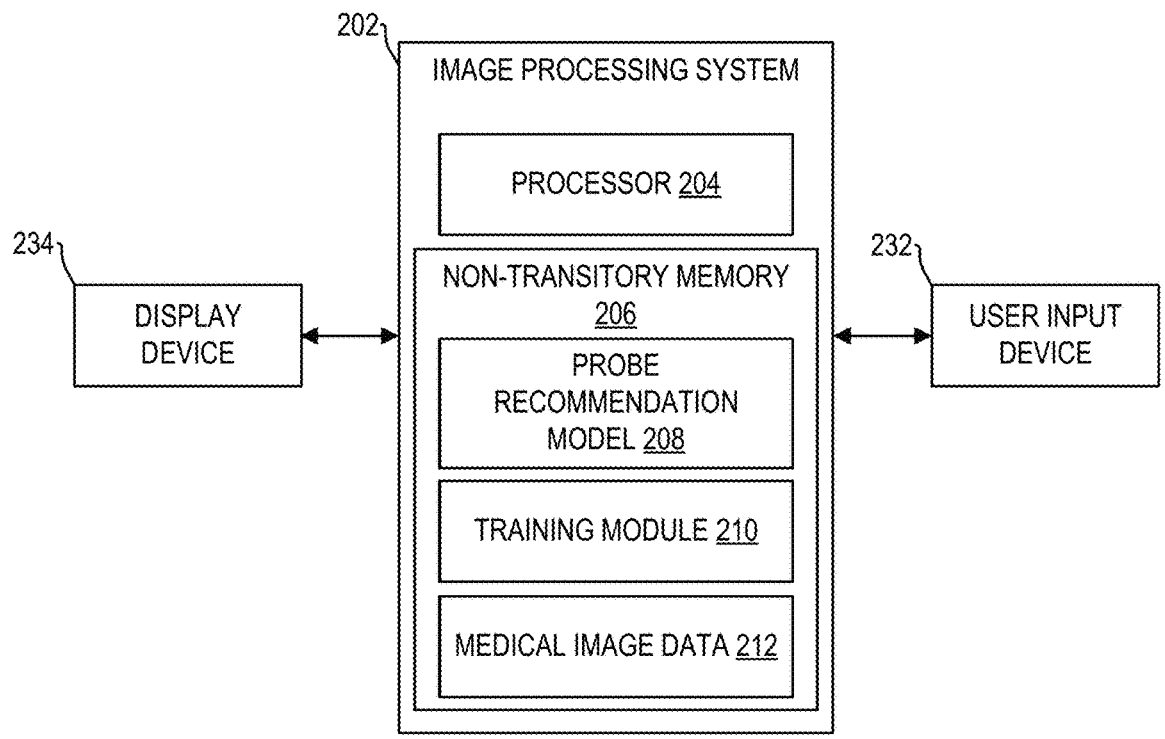
FIG. 2 is a block diagram showing an example image processing system including a probe recommendation model.

Referring to FIG. 2, image processing system 202 is shown, in accordance with an exemplary embodiment. In some embodiments, image processing system 202 is incorporated into a medical imaging system, such as the ultrasound imaging system 100 of FIG. 1. In some embodiments, at least a portion of image processing system 202 is disposed at a device (e.g., edge device, server, etc.) communicably coupled to a medical imaging system via wired and/or wireless connections. In some embodiments, at least a portion of image processing system 202 is disposed at a separate device (e.g., a workstation) which can receive images from a medical imaging system or from a storage device which stores the images generated by a medical imaging system. Image processing system 202 may be operably/communicatively coupled to a user input device 232 and a display device 234.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store a probe recommendation model 208, a training module 210, and medical image data 212. Probe recommendation model 208 may include a machine learning model, such as a deep learning network, comprising a plurality of weights and biases, activation functions, loss functions, gradient descent algorithms, and instructions for implementing the deep neural network to process input ultrasound images. Probe recommendation model 208 may include a trained and/or untrained neural network and may further include training routines, or parameters (e.g., weights and biases), associated with the neural network model stored therein. In some examples, only a single probe recommendation model 208 may be included, where the probe recommendation model 208 may be trained in an anatomy-independent manner such that probe recommendations may be output by the probe recommendation model 208 for multiple scan protocols and/or for imaging multiple, different anatomical features. In other examples, more than one probe recommendation model 208 may be included, with each probe recommendation model 208 trained or specific to a particular scan protocol and/or a particular anatomical feature or set of anatomical features. For example, one probe recommendation model may be specific to imaging a kidney, another probe recommendation model may be specific to imaging a heart, etc.

Each probe recommendation model may generate multiple outputs for a given ultrasound image. For example, each probe recommendation model 208 may output multiple user actions (also referred to as probe motion recommendations) to guide an operator of an ultrasound probe to scan multiple scan planes. The user action may include the maneuvering of the probe by an operator prior to and/or during acquisition of the image. The user action may include translation and/or rotation (roll, pitch, and yaw) of the ultrasound probe, which are usually determined using external sensors such as inertial motion units (IMUs). However, IMUs or other sensors may be expensive, prone to drift, take up packaging space in the ultrasound probe, or exhibit other issues that limit their usefulness in an ultrasound imaging environment. Thus, the probe recommendation model 208 may determine the user action/user motion of the ultrasound probe without external sensors. The probe recommendation model 208 may use as input a current ultrasound image, which may include a source scan plane (e.g., not a target scan plane) or a current target scan plane. Based on the current image, the probe recommendation model 208 may output the movement of the ultrasound probe in six degrees (e.g., translation in 3 dimensions as well as roll, pitch, and yaw) in order to move the ultrasound probe from the current location (at which the current image was acquired) to multiple, different locations to image the two or more target scan planes.

Further, while the probe recommendation model 208 has been described herein has using 2D ultrasound images as input, in some examples the probe recommendation model 208 may use 3D ultrasound data instead of or in addition to 2D images. Further still, while the probe recommendation model 208 has been described herein as being trained to analyze ultrasound images to determine recommendations for movement of an ultrasound probe, a similar approach could be taken to generate recommendations for other imaging modalities, particularly hand-held or otherwise easily manipulated imaging modalities, such as optical imaging devices/visible light cameras (e.g., included as part of an endoscope), X-ray/fluoroscopy scanners, near infrared (NIR) spectroscopy scanners, and optical coherence tomography (OCT) scanners.

Non-transitory memory 206 may further include training module 210, which comprises instructions for training probe recommendation model 208. Non-transitory memory 206 may further store medical image data 212, such as ultrasound images. The medical image data 212 may store medical images, ground truth output, iterations of machine learning model output, and other types of medical image data that may be used to train the probe recommendation model 208. In some embodiments, medical image data 212 may store medical images and ground truth output in an ordered format, such that each medical image is associated with one or more corresponding ground truth outputs.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, to generate ground truth for training the model, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

FIG. 3 shows a simplified model of a volumetric ultrasound ROI 300 including a source scan plane and two target scan planes. The volumetric ultrasound ROI 300 has within it three scan planes: a source scan plane 302 which is currently being imaged by an ultrasound operator, a first target scan plane 304, and a second target scan plane 306. Within the volumetric ultrasound ROI 300, the first target scan plane 304 is superior to (e.g. above) the second target scan plane 306. A probe recommendation model, such as the probe recommendation model 208 of FIG. 2, may be used to give instructions to an ultrasound operator in order to image the two target scan planes starting from the position of the ultrasound probe when the source scan plane 302 was imaged. It should be noted that although the source scan plane 302 is shown as being sandwiched between the first target scan plane 304 and the second target scan plane 306, it may instead be located above both target planes or below both target planes in this simplified example.

The ultrasound operator may be controlling the ultrasound probe according to a scan protocol that dictates images from both the first target scan plane 304 and the second target scan plane 306 be acquired in a sequence. If the source scan plane 302 is superior to both target scan planes, a feasible sequence of probe recommendations would be to move the probe down to the first target scan plane 304 and then to move the probe down to the second target scan plane 306. In this way, both target planes may be imaged. Likewise, if the source scan plane 302 is inferior to (e.g. below) both target scan planes, a logical probe recommendation sequence would be to move the probe up to the second target scan plane 306 and up to the first target scan plane 304.

If, as in the case depicted in FIG. 3, the source scan plane 302 is in between the target scan planes, one feasible case is to move the probe up to reach the first target scan plane 304 followed by a recommendation to the move the probe down to reach the second target scan plane 306. Traditional methods, which may not take into account the vertical ordering of the target scan planes, may also suggest an infeasible sequence of probe movements, namely moving the probe down to reach the first target scan plane 304 and up to reach the second target scan plane 306.

Thus, the probe recommendation model described herein may output a joint recommendation for moving the ultrasound probe to scan two or more target scan planes rather than two independent recommendations, which may reduce or prevent the infeasible or inefficient recommendations described above. The probe recommendation model may be trained to follow anatomical spatial consistencies via the training data used to train the model and/or the loss functions used to train the model. By adding anatomical consistency within the training data or penalizing anatomical inconsistency within the loss function, the infeasible set of probe recommendations may be eliminated or weighted down in the prediction space, meaning that the probe recommendation model would be less likely to recommend infeasible or inefficient probe motions.

In this way, multiple probe motions to guide a user to multiple target scan planes may be output simultaneously by a single probe recommendation model. The multiple probe motions may be independent/separate motions and the user may choose to follow any one of the recommendations to get to the corresponding target scan plane. The benefit of providing all the probe motion recommendations simultaneously is that mutual consistency of recommended motions will ensure correctness of all of the recommendations. In contrast, as explained above, multiple separate models may result in one or more of the models outputting an erroneous recommendation that is not detected or corrected, which may lead to operator confusion and frustration.

FIG. 4 schematically shows a process 400 for the generation of loss terms originating from anatomical consistency enforcement. Process 400 takes as input one or more ultrasound images, such as image 402. Image 402 may be an ultrasound image from a given source scan plane (e.g., not a target scan plane) and may be part of a training data set that also includes two or more ground truth transformations, with each ground truth transformation indicating a probe motion (or set of probe motions) to image a respective target scan plane. Image 402 is input into a deep learning network 404, which may output a plurality of transformations 406. Deep learning network 404 may be a non-limiting (untrained or partially trained) example of the probe recommendation model 208. Each transformation of the plurality of transformations 406 represents a probe motion recommendation for moving the probe from a position where the scan plane of the input image 402 is imaged to one of several target scan planes.

A plurality of loss functions may be calculated during training of the deep learning network 404. The loss functions may include a respective loss function between each transformation of the plurality of transformations and a corresponding ground truth transformation. Further, the loss functions may include a respective loss function between each pair of transformations of the plurality of transformations 406. For example, a first loss function 408 may be generated between a first transformation $\hat{Y}_{SP1}$ between the input image 402 and a first target scan plane (SP1) and a second transformation $\hat{Y}_{SP2}$ between the input image 402 and a second target scan plane (SP2). A second loss function 410 may be generated between the second transformation and a third transformation $\hat{Y}_{SP3}$ between the input image 402 and a third target scan plane (SP3). The first and second loss functions 408, 410 may enforce the anatomical spatial consistency of the scan planes. The loss functions may include categorical cross entropy or mean square error loss functions, for example. The loss term can have a penalty term for infeasible combinations. These infeasible combinations may be determined a priori, as the mutual transformations between target scan planes is known.

FIG. 5 is a flow chart illustrating an example method 500 for generating and outputting joint probe motion recommendations according to an embodiment of the present disclosure. Method 500 is described with regard to the systems and components of FIGS. 1-2, though it should be appreciated that the method 500 may be implemented with other systems and components without departing from the scope of the present disclosure. Method 500 may be carried out according to instructions stored in non-transitory memory of a computing device, such as image processing system 202 of FIG. 2.

At 502, ultrasound images are acquired and displayed on a display device. For example, the ultrasound images of a subject may be acquired with the ultrasound probe 106 of FIG. 1 and displayed to an operator via display device 118. The images may be acquired and displayed in real time or near real time, and may be acquired with default or user-specified scan parameters (e.g., default depth, frequency, etc.). At 504, method 500 determines if probe motion recommendations (e.g., guidance) have been requested. Probe motion recommendations may be requested by a user (e.g., the operator) via user input (e.g., a user may select a "recommendations" button on a graphical user interface), or probe motion recommendations may be requested automatically as part of a scan protocol that the operator may be following in order to image the subject. For example, the operator may select a scan protocol from a menu of scan protocols prior to or during imaging of the subject. The scan protocol may include a list of scan planes and/or anatomical features that are to be imaged, preset scan parameters that are applied to acquire the images, and/or other features. Further, the request to provide probe motion recommendations may include an indication of the anatomy that is being imaged or is to be imaged (e.g., the kidney).

If probe motion recommendations have not been requested, method 500 continues to acquire and display ultrasound image frames, until imaging is terminated by the operator or probe motion recommendations are requested. If probe motion recommendations are requested, method 500 proceeds to 506 to determine target scan planes to be imaged based on the scan protocol. As explained above, the scan protocol may include a list of scan planes that are to be imaged and the target scan planes may be the next scan planes on the list of scan planes (e.g., the scan planes that have yet to be imaged). However, in other examples, the target scan planes may be determined based on user input or another suitable mechanism.

At 508, the current frame (e.g., the most recently acquired image frame) is entered into a probe recommendation model. The probe recommendation model may be the probe recommendation model 208 of FIG. 2. The current frame may include a source scan plane (e.g., not one of the target scan planes from the scan protocol) and be selected based on a frequency of generating probe motion recommendations (e.g., the frequency may be every fifteenth frame and the current frame may be the fifteenth frame since a previous recommendation was generated). In other examples, the current frame may be selected based on the current frame being a frame acquired while the probe was held stationary or selected based on user input.

The probe recommendation model may be trained to output joint probe motion recommendations to guide the operator to move the probe from a first location (e.g., where the current frame was acquired) to a plurality of additional locations were a plurality of target scan planes can be imaged. For example, the plurality of additional locations may include at least a second location (where a first frame of a first target scan plane may be acquired) and a third location (where a second frame of a second target scan plane may be acquired). Accordingly, at 516, the joint probe motion recommendations are output to the operator by displaying the recommendations on a display device (e.g., display device 118). In some examples, additionally or alternatively, the probe motion recommendations may be output via an audible output mechanism (e.g., via a speaker), haptic feedback, or another suitable mechanism.

At 518, the above-described process of determining probe motion recommendations is repeated. The process may be repeated at a given frequency (e.g., for each Nth frame of ultrasound images). For example, after acquisition of the current frame, fifteen additional ultrasound frames may be acquired, and the fifteenth frame may be designated as the new current frame. The new current frame may be used to determine a new or updated probe motion recommendation according to the process described above, e.g., the new current frame may be entered as input to the probe recommendation model. Each time the determined probe motion recommendations change, updated recommendations may be output to the operator (e.g., displayed on the display device). In other examples, the process may be repeated each time motion of the probe is detected, or each time motion of the probe is detected and then the motion ends. In still further examples, the process may be repeated in response to a request to generate new probe motion recommendations.

At 520, method 500 includes determining if the operator is following the probe motion recommendations. The operator may be determined to be following the probe motion recommendations when, after outputting one or more probe motion recommendations, subsequent user actions and anatomy views indicate that the probe was moved as recommended. The operator may be determined not to be following the probe motion recommendations when, after outputting one or more probe motion recommendations, subsequent user actions and anatomy views indicate that the probe was not moved as recommended. If it is determined that the operator is not following the probe motion recommendations, method 500 proceeds to 522 to confirm that the target scan planes are the correct target scan planes and/or output additional guidance. For example, if the operator is not following the probe motion recommendations, the operator may have decided to image a scan plane that is different than the target scan planes and thus the probe motion recommendations may be inaccurate. Thus, a notification may be output (e.g., to the display device) asking the operator to confirm the target scan planes. In some examples, additionally or alternatively, additional guidance may be output (e.g., to the display device) in order to help guide the operator to the target scan planes. For example, there may be multiple paths to get to the target scan planes. When user is not following the recommended probe motions, a different set/combination of probe motion recommendations (alternate mode) can be used to reach the same scan planes. In some examples, the frequency of the output probe motion recommendations may be increased to provide more granular recommendations. For example, rather than outputting probe motion recommendations every 15 frames, as explained above, the probe motion recommendations may be output every 10 frames. Further, in some examples, the operator may be instructed to stop the current probe motion/user action (e.g., "stop rotating the probe"), which may further assist the operator by notifying the operator of motion errors rather than simply providing guidance of where to move the probe. This may also include notifying the operator that the operator is not following the probe motion recommendations.

If at 520 it is determined that the operator is following the probe motion recommendations, method 500 proceeds to 524 to determine if one or more new target scan planes have been indicated, via user input and/or via the scan protocol. For example, once one or more images of the target scan planes have been obtained, the scan protocol may indicate additional image(s) be obtained in a different scan plane. If a new target scan plane has not been indicated, method 500 proceeds to 526 to determine if the scan protocol is complete. For example, the scan protocol may be complete if all target scan planes/anatomical features dictated by the scan protocol have been imaged and/or if the operator indicates via user input that the scan protocol is complete or that the current imaging session is done. If the scan protocol is complete, method 500 returns. If the scan protocol is not complete, method 500 returns to 518 to continue to acquire images, enter the images into the probe recommendation model, and output appropriate probe motion recommendations.

If at 524 it is determined that one or more new target scan planes have been indicated, method 500 proceeds to 528 to determine probe motion recommendations for guiding the operator to the new target scan plane(s), where the probe motion recommendations are determined based on the new target scan plane(s), similar to the process for generating probe motion recommendations for the previous target scan planes as described above. The new probe recommendations should also be generated with anatomical consistency enforced. Upon outputting the probe motion recommendations, method 500 returns to 520 to determine if the operator is following the probe motion recommendations. In this way, probe motion recommendations may be generated for each set of target scan planes of the scan protocol, until scanning is complete. Further, once the operator moves the ultrasound probe to a location to image a first target scan plane, updated probe motion recommendations may be provided to guide the operator to move the ultrasound probe from the location to one or more additional locations to image the remaining target scan planes. This process may repeat until all the target scan planes have been imaged.

Thus, the probe recommendation model disclosed herein may be deployed in order to generate multiple probe motion recommendations to image multiple target scan planes. As explained above, an ultrasound image of a source scan plane may be entered as input to a probe recommendation model. The ultrasound image may be acquired with an ultrasound probe at a first location relative to a patient, and the probe recommendation model may be trained to output a set of recommendations to move the ultrasound probe from the first location to each of a plurality of additional locations at which a plurality of target scan planes can be imaged. The set of recommendations output by the model may be displayed on a display device. The set of recommendations may comprise a plurality of transformations representing respective probe motions to move the ultrasound probe from the first location to each additional location. As will be explained in more detail below with respect to FIG. 6, the probe recommendation model may be trained with a plurality of training data sets, each training data set including a training image of the source scan plane and a set of ground truth transformations, each ground truth transformation mapping the training image to a respective target scan plane. The probe recommendation model may be configured to output, for each input training data set, a plurality of transformations representing respective probe motions to image each target scan plane starting from the source scan plane. The probe recommendation model may be trained with a first plurality of loss functions determined based on the plurality of transformations relative to the set of ground truth transformations and a second plurality of loss functions determined on the plurality of transformations relative to each other (e.g., a first loss function of the second plurality of loss functions may be determined based on a first output transformation relative to a second output transformation, etc.). The set of ground truth transformations may be generated in a suitable manner, such as based on a respective position within an ultrasound volume of each target scan plane relative to the source scan plane and/or based on output from one or more probe motion sensors of the ultrasound probe as the ultrasound probe is moved from the source scan plane to each target scan plane.

As an example, the ultrasound system described herein (e.g., the system of FIG. 1) may be controlled to acquire an ultrasound image of a source scan plane with the ultrasound probe at a first location relative to a patient. The ultrasound image may be entered as input to a probe recommendation model trained to output a first recommendation to move the ultrasound probe from the first location to a second location at which a first target scan plane can be imaged and a second recommendation to move the ultrasound probe from the first location to a third location at which a second target scan plane can be imaged. The first recommendation and the second recommendation may be displayed on a display (e.g., coupled to or included as part of the ultrasound system). The probe recommendation model may be trained to output a first transformation representing a first probe motion to move the ultrasound probe from the first location to the second location and a second transformation representing a second probe motion to move the ultrasound probe from the first location to the third location, where the first recommendation comprises the first transformation and the second recommendation comprises the second transformation. The probe recommendation model may be trained with a plurality of training data sets, each training data set including a training image of the source scan plane, a first ground truth transformation mapping the training image to the first target scan plane, and a second ground truth transformation mapping the training image to the second target scan plane. The probe recommendation model may be configured to output, for each input training data set, a first output transformation representing a first probe motion to image the first target scan plane starting from the source scan plane and a second output transformation representing a second probe motion to image the second target scan plane starting from the source scan plane. The loss functions that may be calculated and used to train the probe recommendation model may include a first loss function determined based on the first output transformation relative to the first ground truth transformation, a second loss function based on the second output transformation relative to the second ground truth transformation, and a third loss function based on the first output transformation relative to the second output transformation.

FIG. 6 shows a method 600 for the generation of training data and the training of the probe motion recommendation model, such as the probe recommendation model 208. Method 600 may be carried out according to instructions stored in non-transitory memory, such as within the training module 210 of the image processing system 202. At 602, method 600 includes generating training data. The training data may include a plurality of sets of training data. As indicated at 604, each training set includes a training image of a source scan plane, N target scan planes, and N ground truth transformation matrices. For example, for training the probe recommendation model to generate probe motion recommendations/guidance for a scan protocol including two target scan planes, each training data set may include a training image of a source scan plane, an indication of the two target scan planes, and two ground truth transformation matrices. Each training data set may include a different training image. In some examples, a first subset of the training data sets may include training images of a first source scan plane, a second subset of the training data sets may include training images of a second, different source scan plane, a third subset of the training data sets may include training images of a third source scan plane, and so forth, such that training data sets are generated for each possible source scan plane of a given imaging volume. The training images may be selected from a volume(s) of ultrasound data where a given anatomical feature (e.g., the kidney) is imaged, with each training image corresponding to a respective plane of the volume(s).

Each ground truth transformation matrix may represent a probe motion (or set of motions) to move an ultrasound probe from a location where the source scan plane is imaged to a respective location where one of the target planes can be imaged. For example, when the probe recommendation model is trained to output guidance for imaging two target scan planes as described above, a first ground truth transformation matrix may represent probe motion to move a probe from a first location where the source scan plane is imaged to a second location where a first target scan plane can be imaged and a second transformation matrix may represent probe motion to move the probe from the first location where the source scan plane is imaged to a third location where a second target scan plane can be imaged. In some examples, the ground truth transformation matrices may be generated based on the position of the target scan planes relative to the source scan plane in the ultrasound volume(s). In some examples, the ground truth transformation matrices may be generated based on the output from one or more probe motion sensors arranged on an ultrasound probe, which may be moved from the first location to the second location by an expert (e.g., trained sonographer) to generate probe motion output that can be transformed to the first ground truth transformation matrix, from the first location to the third location to generate probe motion output that can be transformed to the second ground truth transformation matrix, and from the first location to any additional locations to generate probe motion output that can be transformed to additional ground truth transformation matrices corresponding to additional target scan planes. In some examples, the ground truth transformation matrices may be generated by experts (e.g., trained sonographers) who may manually generate the transformations.

Generating the training data may include enforcing anatomical consistency within the ground truth transformation matrices themselves. This may include, for example, excluding those transformation matrices which produce infeasible sequences of transformations, such as the infeasible sequence discussed with regards with FIG. 3. Excluding the infeasible sequences from the ground truth data may cause the probe recommendation model to disfavor or exclude these outcomes as well.

At 608, method 600 includes enter the training data into the untrained probe recommendation model. For example, the training image and each ground truth transformation matrix may be concatenated or entered as separate layers to an input layer of the untrained (or partially trained) probe recommendation model.

At 610, method 600 includes training the probe recommendation model using the ground truth transformation matrices. Training the probe recommendation model based on the ground truth transformation matrices may include, as indicated at 612, pairing transformation matrices between each plane in a sequence of planes. The first plane in the sequence may be the source scan plane, corresponding to the training image. The remaining planes may be a sequence of the target scan planes. The transformation matrices may be ground truth transformation matrices, which may be generated as explained above.

At 614, method 600 includes calculating one or more loss functions and optionally penalizing anatomical inconsistencies. As discussed above with respect to FIG. 4, loss terms may be generated to penalize inconsistencies between transformation matrices. Penalizing anatomical inconsistencies in the loss functions may allow for less training data to be used to train the probe recommendation model. A total loss function may be computed by, for example, $$L_{total} = \sum_i L(Y_{SPi}, \hat{Y}_{SPi}) + \sum_{j,k \neq j} L_{cons}(\hat{Y}_{SPj}, \hat{Y}_{SPk}).$$

In this (non-limiting) example of a loss function, each $\hat{Y}_{SPi}$ represents an output transformation matrix from the source scan plane to the target scan plane output by the probe recommendation model. Each $Y_{SPi}$ represents a ground truth transformation from the source scan plane to a target scan plane SPi. The first summation term in the total loss calculation represents errors between transformations output by the probe recommendation model and one or more ground truth matrices. The second summation term represents anatomical consistency enforcement through a loss term, such as a loss between a first output transformation matrix output by the model (e.g., from the source scan plane to a first target scan plane) and a second output transformation matrix output by the model (e.g., from the source scan plane to a second target scan plane). Similar loss functions may be calculated for each pair of transformation matrices output by the model, such that if a third transformation matrix was output by the model (e.g., from the source scan plane to a third target scan plane), a loss function would be calculated between the first output transformation matrix and the third output transformation matrix and a loss function would be calculated between the second output transformation matrix and the third output transformation matrix.

At 616, method 600 includes updating the weights and biases of the probe recommendation model based on the loss (e.g., based on the total loss as calculated above). In one example, this may comprise evaluating the gradient of the loss function in order to perform a gradient descent algorithm and/or updating the model via backpropagation.

Thus, training the probe recommendation model may include generating training data including a plurality of training data sets, each training data set including a training image of a source scan plane, a first ground truth transformation mapping the training image to a first target scan plane, and a second ground truth transformation mapping the training image to a second target scan plane. Training the probe recommendation model may further include entering each training data set as input to a probe recommendation model configured to output, for each input training data set, a first output transformation representing a first probe motion to image the first target scan plane starting from the source scan plane and a second output transformation representing a second probe motion to image the second target scan plane starting from the source scan plane. Training the probe recommendation model may further include updating the probe recommendation model based on a first loss function determined based on the first output transformation relative to the first ground truth transformation, a second loss function based on the second output transformation relative to the second ground truth transformation, and a third loss function based on the first output transformation relative to the second output transformation. The training data may be generated by generating the first ground truth transformation based on a first position within an ultrasound volume of the first target scan plane relative to the source scan plane and generating the second ground truth transformation based on a second position within the ultrasound volume of the second target scan plane relative to the source scan plane. Additionally or alternatively, generating the training data may include generating the first ground truth transformation based on output from one or more probe motion sensors of an ultrasound probe as the ultrasound probe is moved from the source scan plane to the first target scan plane and generating the second ground truth transformation based on output from the one or more probe motion sensors as the ultrasound probe is moved from the source scan plane to the second target scan plane. This above process may be repeated for other source scan planes and other target scan planes, e.g., the plurality of training data sets may be a first plurality of training data sets, the training image may be a first training image, and the source scan plane may be a first source scan plane, a second plurality of training data sets may be generated, each training data set of the second plurality of training data sets including a second training image of a second source scan plane, a third ground truth transformation mapping the second training image to the first target scan plane, and a fourth ground truth transformation mapping the second training image to the second target scan plane. In another example, each training data set further includes a third ground truth transformation mapping the training image to a third target scan plane, and the probe recommendation model is configured to output a third output transformation representing a third probe motion to image the third target scan plane starting from the source scan plane. The probe recommendation model may be further updated based on a fourth loss function based on the third output transformation relative to the third ground truth transformation, a fifth loss function based on the first output transformation relative to the third output transformation, and a sixth loss function based on the second output transformation relative to the third output transformation.

FIG. 7 shows an example chart 700 illustrating probe motion recommendations that may be output to instruct an operator to move from a source scan plane to a plurality of target planes while imaging a selected anatomical feature, herein the kidney. Chart 700 includes a plurality of source scan planes 702, represented along a left-most column of chart 700. The source scan planes 702 include several example source scan planes, such as a source scan plane 704. The source scan planes, such as source scan plane 704, are represented by ultrasound imagery taken from the plane. The location (e.g. in 3D space) of each source scan plane may be identified, for example, through anatomical landmarks visible in the frame.

Chart 700 further includes a plurality of target scan planes 706 depicted along a top-most row of chart 700. The target scan planes 706, such as target scan plane 708, are also represented here as ultrasound imagery. The target scan plane 708 is shown as an ultrasound image of the right kidney from the mid-axial plane, which is one of many standard scan planes of the right kidney.

The probe motion recommendation model, trained using method 600, may be used to generate a plurality of probe motion recommendations, which may be employed in a cyclical process, such as method 500. For example, referring to probe motion recommendations that may be output based on the source scan plane 704 and the target scan planes 706, a first probe motion recommendation 701 may include a recommendation to "sweep up" to move the probe from the source scan plane 704 to the target scan plane 708. A second probe motion recommendation 703 may include a recommendation to "rotate CW" (e.g., rotate the probe clockwise) to move the probe from the source scan plane 704 to a second target scan plane 710. A third probe motion recommendation 705 may include a recommendation to "rotate CW" (e.g., rotate the probe clockwise) to move the probe from the source scan plane 704 to a third target scan plane 712. The probe recommendation model may be trained to output the probe motion recommendations such that the operator may follow selected probe motion guidance to image one of the target scan planes. Once that target scan plane is imaged, new probe motion recommendations may be output to guide the operator to image the remaining target scan planes. In this way, during inference when the probe motion recommendation model is deployed, the probe motion recommendation model may output a set of separate, individual probe motion recommendations, with each probe motion recommendation corresponding to a different target scan plane. However, to reduce errors in the probe motion recommendations, the probe recommendation model may be trained jointly, taking into consideration all the target scan planes.

A technical effect of generating multiple probe motion recommendations with a single probe recommendation model is that probe motion recommendation errors may be reduced by enforcing anatomical spatial consistency on the probe recommendation model during training of the model, thereby improving image quality, reducing operator frustration, and lowering the amount of time to complete a scan protocol. Fewer unnecessary probe motions may be performed, which may result in fewer ultrasound frames being acquired, which may improve the efficiency of the ultrasound imaging system.

The disclosure also provides support for a method, comprising: obtaining an ultrasound image of a source scan plane, the ultrasound image acquired with an ultrasound probe at a first location relative to a patient, entering the ultrasound image as input to a probe recommendation model trained to output a set of recommendations to move the ultrasound probe from the first location to each of a plurality of additional locations at which a plurality of target scan planes can be imaged, and displaying the set of recommendations on a display device. In a first example of the method, the probe recommendation model is trained to output a plurality of transformations representing respective probe motions to move the ultrasound probe from the first location to each additional location, and wherein the set of recommendations comprises the plurality of transformations. In a second example of the method, optionally including the first example, the probe recommendation model is trained with a plurality of training data sets, each training data set including a training image of the source scan plane and a set of ground truth transformations, each ground truth transformation mapping the training image to a respective target scan plane. In a third example of the method, optionally including one or both of the first and second examples, the probe recommendation model is configured to output, for each input training data set, a plurality of transformations representing respective probe motions to image each target scan plane starting from the source scan plane. In a fourth example of the method, optionally including one or more or each of the first through third examples, the probe recommendation model is trained with a first plurality of loss functions determined based on the plurality of transformations relative to the set of ground truth transformations and a second plurality of loss functions determined on the plurality of transformations relative to each other. In a fifth example of the method, optionally including one or more or each of the first through fourth examples, the set of ground truth transformations is generated based on a respective position within an ultrasound volume of each target scan plane relative to the source scan plane. In a sixth example of the method, optionally including one or more or each of the first through fifth examples, the set of ground truth transformations is generated based on output from one or more probe motion sensors of the ultrasound probe as the ultrasound probe is moved from the source scan plane to each target scan plane.

The disclosure also provides support for an ultrasound imaging system, comprising: an ultrasound probe, a display, a processor, and memory storing instructions executable by the processor to: acquire an ultrasound image of a source scan plane with the ultrasound probe at a first location relative to a patient, enter the ultrasound image as input to a probe recommendation model trained to output a first recommendation to move the ultrasound probe from the first location to a second location at which a first target scan plane can be imaged and a second recommendation to move the ultrasound probe from the first location to a third location at which a second target scan plane can be imaged, and display the first recommendation and the second recommendation on the display. In a first example of the system, the probe recommendation model is trained to output a first transformation representing a first probe motion to move the ultrasound probe from the first location to the second location and a second transformation representing a second probe motion to move the ultrasound probe from the first location to the third location, and wherein the first recommendation comprises the first transformation and the second recommendation comprises the second transformation. In a second example of the system, optionally including the first example, the probe recommendation model is trained with a plurality of training data sets, each training data set including a training image of the source scan plane, a first ground truth transformation mapping the training image to the first target scan plane, and a second ground truth transformation mapping the training image to the second target scan plane. In a third example of the system, optionally including one or both of the first and second examples, the probe recommendation model is configured to output, for each input training data set, a first output transformation representing a first probe motion to image the first target scan plane starting from the source scan plane and a second output transformation representing a second probe motion to image the second target scan plane starting from the source scan plane. In a fourth example of the system, optionally including one or more or each of the first through third examples, the probe recommendation model is trained with a first loss function determined based on the first output transformation relative to the first ground truth transformation, a second loss function based on the second output transformation relative to the second ground truth transformation, and a third loss function based on the first output transformation relative to the second output transformation. In a fifth example of the system, optionally including one or more or each of the first through fourth examples, the first ground truth transformation is generated based on a first position within an ultrasound volume of the first target scan plane relative to the source scan plane and the second ground truth transformation is generated based on a second position within the ultrasound volume of the second target scan plane relative to the source scan plane. In a sixth example of the system, optionally including one or more or each of the first through fifth examples, the first ground truth transformation is generated based on output from one or more probe motion sensors of the ultrasound probe as the ultrasound probe is moved from the source scan plane to the first target scan plane and the second ground truth transformation is generated based output on from the one or more probe motion sensors as the ultrasound probe is moved from the source scan plane to the second target scan plane.

The disclosure also provides support for a method, comprising: generating training data including a plurality of training data sets, each training data set including a training image of a source scan plane, a first ground truth transformation mapping the training image to a first target scan plane, and a second ground truth transformation mapping the training image to a second target scan plane, enter each training data set as input to a probe recommendation model configured to output, for each input training data set, a first output transformation representing a first probe motion to image the first target scan plane starting from the source scan plane and a second output transformation representing a second probe motion to image the second target scan plane starting from the source scan plane, and updating the probe recommendation model based on a first loss function determined based on the first output transformation relative to the first ground truth transformation, a second loss function based on the second output transformation relative to the second ground truth transformation, and a third loss function based on the first output transformation relative to the second output transformation. In a first example of the method, generating the training data includes generating the first ground truth transformation based on a first position within an ultrasound volume of the first target scan plane relative to the source scan plane and generating the second ground truth transformation based on a second position within the ultrasound volume of the second target scan plane relative to the source scan plane. In a second example of the method, optionally including the first example, generating the training data comprises generating the first ground truth transformation based on output from one or more probe motion sensors of an ultrasound probe as the ultrasound probe is moved from the source scan plane to the first target scan plane and generating the second ground truth transformation based on output from the one or more probe motion sensors as the ultrasound probe is moved from the source scan plane to the second target scan plane. In a third example of the method, optionally including one or both of the first and second examples, the plurality of training data sets is a first plurality of training data sets, the training image is a first training image, and the source scan plane is a first source scan plane, and further comprising generating a second plurality of training data sets, each training data set of the second plurality of training data sets including a second training image of a second source scan plane, a third ground truth transformation mapping the second training image to the first target scan plane, and a fourth ground truth transformation mapping the second training image to the second target scan plane. In a fourth example of the method, optionally including one or more or each of the first through third examples, each training data set further includes a third ground truth transformation mapping the training image to a third target scan plane, the probe recommendation model is configured to output a third output transformation representing a third probe motion to image the third target scan plane starting from the source scan plane, and updating the probe recommendation model further includes updating the probe recommendation model based on a fourth loss function based on the third output transformation relative to the third ground truth transformation, a fifth loss function based on the first output transformation relative to the third output transformation, and a sixth loss function based on the second output transformation relative to the third output transformation.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. An ultrasound imaging system, comprising:
an ultrasound probe;
a display;
a processor; and
memory storing instructions executable by the processor to:
  acquire a first ultrasound image of a source scan plane with the ultrasound probe at a first location relative to a patient;
  enter the first ultrasound image as input to a probe recommendation model trained to output a first recommendation to move the ultrasound probe from the first location to a second location at which a first target scan plane can be imaged and a second recommendation to move the ultrasound probe from the first location to a third location at which a second target scan plane can be imaged;
  display the first recommendation and the second recommendation on the display; and
  acquire a second ultrasound image of the first target scan plane at the second location with the ultrasound probe,
  wherein the probe recommendation model is trained with a first loss function determined based on a first output transformation relative to a first ground truth transformation, a second loss function based on a second output transformation relative to a second ground truth transformation, and a third loss function based on the first output transformation relative to the second output transformation.

2. The system of claim 1, wherein the probe recommendation model is trained with a plurality of training data sets, each training data set including a training image of the source scan plane, the first ground truth transformation mapping the training image to the first target scan plane, and the second ground truth transformation mapping the training image to the second target scan plane.

3. The system of claim 2, wherein the probe recommendation model is configured to output, for each input training data set, the first output transformation representing a first probe motion to image the first target scan plane starting from the source scan plane and the second output transformation representing a second probe motion to image the second target scan plane starting from the source scan plane.

4. The system of claim 2, wherein the first ground truth transformation is generated based on a first position within an ultrasound volume of the first target scan plane relative to the source scan plane and the second ground truth transformation is generated based on a second position within the ultrasound volume of the second target scan plane relative to the source scan plane.

5. The system of claim 2, wherein the first ground truth transformation is generated based on output from one or more probe motion sensors of the ultrasound probe as the ultrasound probe is moved from the source scan plane to the first target scan plane and the second ground truth transformation is generated based on output from the one or more probe motion sensors as the ultrasound probe is moved from the source scan plane to the second target scan plane.

6. The system of claim 1, wherein training the probe recommendation model includes updating weights and biases of the probe recommendation model based on a total loss, and
wherein the total loss includes the first loss function, the second loss function, and the third loss function.

7. The system of claim 1, wherein the first recommendation and the second recommendation take into account a vertical ordering of the first target scan plane and the second target scan plane.

8. The system of claim 1, wherein the probe recommendation model is further trained to follow anatomical spatial consistencies via training data that includes images of scan planes and transformations between the scan planes.

9. The system of claim 1, wherein the first recommendation and the second recommendation are output simultaneously by the probe recommendation model, and wherein the probe recommendation model is a single probe recommendation model.

10. The system of claim 8, wherein training the probe recommendation model with the training data eliminates instances of infeasible probe movement recommendations.

11. The system of claim 1, wherein the memory storing instructions is further executable by the processor to:
acquire a third ultrasound image at the third location of the second target scan plane with the ultrasound probe.

12. The system of claim 11, wherein the first recommendation and the second recommendation are a feasible sequence of probe recommendations, and wherein the third ultrasound image is acquired sequentially after the second ultrasound image.

* * * * *